United States Patent [19]
Zeikus et al.

[11] Patent Number: 4,732,855
[45] Date of Patent: Mar. 22, 1988

[54] PROCESS FOR PREPARATION OF PROPIONIC ACID

[75] Inventors: Joseph G. Zeikus; Thomas E. Thompson, both of Madison, Wis.

[73] Assignee: Wisconsin Alumni Research Foundation, Madison, Wis.

[21] Appl. No.: 596,263

[22] Filed: Apr. 3, 1984

[51] Int. Cl.$^4$ .......................... C12N 1/38; C12P 7/52; C12R 1/01
[52] U.S. Cl. .................................. 435/141; 435/244; 435/801; 435/822
[58] Field of Search ............... 435/141, 244, 253, 801, 435/822

[56] References Cited

U.S. PATENT DOCUMENTS 4,400,470  8/1983  Zeikus et al. ...................... 435/162

OTHER PUBLICATIONS

Schink, B., Thompson, T. E. and Zeikus, J. G., (1982), J. Gen. Microbiol., 128, 2771–2779.
Kerby, R., Niemczura, W., and Zeikus, J. G., (1983), J. Bacteriol., 155, 1208–1218.
Zeikus, J. G., Fuchs, G., Kenealy, W., and Thauer, R. K., (1977), J. Bacteriol., 132, 604–613.
Lamed, R. and Zeikus, J. G., (1980), J. Bacteriol., 144, 569–578.
Schink, B., Lupton, F. S. and Zeikus, J. G., (1983), Appl. Environ. Microbiol., 45, 1491–1500.
Zeikus, J. G., (1983), Microbes in Their Natural Environments, Soc. Gen. Microbiol., Cambridge University Press.
Zeikus, J. G., (1980), Ann. Rev. Microbiol., 34, 423–464.

Primary Examiner—Elizabeth Weimar
Attorney, Agent, or Firm—Quarles & Brady

[57] ABSTRACT

An improved process for the production of propionic acid comprises cultivating a propionic acid-producing bacterium anaerobically in a medium which contains a simple carbohydrate, which can be converted by the bacterium to pyruvate, as well as essential minerals, vitamins, and growth factors under an overpressure of hydrogen which is effective to cause a hydrogenase produced by the bacterium to suppress the oxidation of pyruvate to acetate and carbon dioxide and to promote the formation of propionic acid.

8 Claims, No Drawings

PROCESS FOR PREPARATION OF PROPIONIC ACID

FIELD OF THE INVENTION

The present invention generally relates to microbial processes for the preparation of propionic acid or propionate. More particularly, it relates to an improvement in a known microbial process which results in greater yields of propionic acid or propionate.

BACKGROUND OF THE INVENTION

The propagation of microbial cells to obtain fermentation products, including propionic acid, is well known. Recently, there has been considerable interest in fermentation processes which can be used to produce chemicals from carbohydrate feed stocks instead of petroleum feed stocks.

In U.S. Pat. No. 4,425,432, a microbial method is disclosed for preparing acetic and butyric acid as fermentation products from carbohydrates. It also is known that Propionibacterium will produce propionate, acetate and carbon dioxide as the major end products of carbohydrate fermentation. For example, *Propionispira arboris* ferments 1.5 moles of glucose into propionate, acetate and carbon dioxide in a 2:1:1 ratio and ferments 3 moles of fumarate into propionate, acetate and carbon dioxide in a 2:1:4 ratio. Since propionic acid or propionate is a more valuable chemical than acetate or carbon dioxide, it obviously would be desirable to develop a microbial process in which propionic acid or propionate production is increased at the expense of acetate and carbon dioxide formation.

SUMMARY OF THE INVENTION

It is an object of the present invention to disclose an improved process for preparing higher yields of propionic acid or propionate than previously obtainable.

In the improved process of the present invention a propionic acid-producing bacterium is cultivated anaerobically in a medium which contains a simple carbohydrate substrate, such as a simple sugar, lactate or fumarate, essential minerals, vitamins and growth factors under an overpressure of hydrogen which suppresses the formation of acetate and carbon dioxide and promotes the formation of propionic acid. The propionic acid or propionate that forms is separated from the fermentation broth and collected.

The propionic acid-producing bacteria which may be employed are those which normally fix nitrogen and produce propionic acid or propionate, acetate and carbon dioxide as the major reduced end products of fermentation and which produce a hydrogenase which in the presence of an overpressure of hydrogen blocks the oxidation of pyruvate to carbon dioxide and acetate. Thus, certain propionic acid producing bacteria species that fix nitrogen, e.g. *Propionibacterium shermanii*, can be included in this group (1,2).

The foregoing and other objects of the invention will become apparent from the description which follows.

PREFERRED EMBODIMENT OF THE INVENTION

In the preferred process of the present invention, *Propionispira arboris*, a propionic acid-producing bacterium, is grown under anaerobic conditions in a culture medium which contains essential vitamins, minerals and growth factors and a simple carbohydrate substrate, preferably glucose, lactate or fumarate, under an overpressure of hydrogen which is effective to cause the hydrogenase produced by the bacterium to suppress the oxidation of pyruvate to acetate and carbon dioxide and increase the yield of propionic acid or propionate.

*Propionispira arboris* is a gram-negative, nitrogen-fixing bacterium which produces a hydrogenase that in the presence of an abundance of hydrogen interferes with the oxidation of pyruvate to carbon dioxide and acetate. The preferred strain of *Propionispira arboris* is 12B4 (ATCC No. 33732).

The temperature of the fermentation may be from about 20° C. to about 60° C. but is preferably conducted at about 30° centigrade in an anaerobic pressure vessel with an initial nitrogen/carbon dioxide (95:5) gas headspace. The hydrogen is added as an overpressure to the headspace after the initial inoculation.

The optimum overpressure of hydrogen to be employed can be readily determined. When the substrate employed is sodium lactate, the use of an overpressure of one atmosphere of hydrogen increases the propionate to acetate ratio from 2:8 to 5:3. When the substrate employed is sodium fumarate and an overpressure of one atmosphere of hydrogen is employed, the propionate to acetate ratio is increased from 2:1 to 6:1. When the substrate is glucose, the ratio is increased from 2:1 to 8:1 with one atmosphere of hydrogen and to 16:1 when two atmospheres of hydrogen are used.

The substrates that may be employed are simple carbohydrates that can be converted by the selected organism to pyruvate and the pyruvate to propionic acid, acetate and carbon dioxide. In addition to glucose, lactate and fumarate other simple carbohydrate substrates including simple sugars (monosaccharides) can be used. The substrates also may be commercial by-products which contain simple carbohydrates such as whey which contains lactose.

The practice of the present invention is further illustrated by the experimental work which is described below.

EXPERIMENTAL MATERIALS AND METHODS

All chemicals used were of reagent grade and were obtained from Mallinckrodt (Paris, Ky.) or Sigma Chemical Co. (St. Louis, Mo.). All gases were obtained from Matheson Scientific (Joliet, Il.) and were scrubbed free of oxygen by passage over heated copper filings. Purified ferredoxin was a gift of L. E. Mortenson (Exxon Corp.).

*Propionispira arboris* strain 12B4 (ATCC #33732) was cultured by fastidious anaerobic techniques on the phosphate buffered mineral salts medium (LPBB medium) as described elsewhere (3). All experiments, except where growth was quantified, were done in 158 ml serum vials that were sealed with butyl rubber bungs and aluminum crimps. The vials contained 50 ml of LPBB medium under a $N_2/CO_2$ (95:5% vol/vol) headspace supplemented with 0.05% yeast extract. A description of the LPBB medium can be found in U.S. Pat. No. 4,425,432 which is incorporated by reference herein.

The carbon and energy sources (glucose, sodium lactate (D,L), or sodium fumarate) were sterilized separately as 10% neutralized solutions and were added to a final concentration of 0.5%. The sodium fumarate solution was filter sterilized. The pH of all culture media was about 7–8. For experiments involving exogenous hydrogen addition, the cultivation vessels were pressurized with 1 or 2 atmospheres of 100% $H_2$ gas. Growth experiments used the same medium conditions but were performed in anaerobic pressure tubes (Bellco, Glass, Vineland, N.J.).

Low levels of hydrogen were quantified in culture vessels by sampling the headspace with a gas tight syringe. After dilution of the sample with hydrogen free air, analysis was performed in a $H_2$ analyzer based on a HgO to Hg vapor conversion technique. Acetate and propionate were quantified by gas chromatographic techniques described elsewhere (3,4).

Cells were mass cultured for enzymological studies in 20 liter glass carboys that contained 15 liters of LPBB medium, 0.05% yeast extract, 0.5% carbon source and a 1 atm of $N_2/CO_2$ (95:5%) headspace. Cells were grown at 37° C. until the late exponential phase and were harvested with a DuPont (Wilmington, Del.) KSB continuous flow centrifuge system. The cells were stored frozen at −80° C. under $N_2$ gas until used. Cell extracts were prepared anaerobically by methods described elsewhere (5). Ferredoxin was removed from cell extracts by anoxic DEAE cellulose treatment (6).

Uptake hydrogenase activity was assayed spectrophotometrically using sealed anoxic glass cuvettes flushed with hydrogen (100% headspace). The cuvettes contained 1 ml of 50 mM tricine buffer (pH 8.0), and either 10 mM methyl viologen (MV), 5 mM benzyl viologen (BV), 100 μM dichlorophenol indophenol (DCPIP), 25 μM methylene blue (MB), 200 μM NAD, or 200 μM NADP. Enough sodium dithionite was added to the cuvette reaction mixtures to remove traces of $O_2$ which resulted in a faint color change caused by dye reduction. The assay was initiated by the addition of cell free extracts. The wavelengths and millimolar extinction coefficients used were methyl viologen, 578 nm, 9.78; benzyl viologen, 578, 8.65; DCPIP, 600, 21; MB, 668, 63; NAD, 340, 6.22; NADP, 340, 6.22. To test for the CO dependent inhibition of hydrogenase activity, the cuvettes contained tricine buffer, methyl viologen, a 1 atm 100% $H_2$ gas phase, and CO was added by gas tight syringe to 9.3% in the headspace. These cuvettes were incubated for 20 min. to allow equilibration of the gas and liquid phases prior to the addition of cell extracts. Hydrogen production activity of hydrogenase in cell extracts was determined in rubber stoppered glass vials (12 ml that contained 5 ml of 50 mM tricine buffer (pH 3.0), a 100% $N_2$ gas headspace, 20 μmol sodium dithionite, and either 20 μmol methyl viologen or 100 μg of purified ferredoxin). Hydrogen was measured by removing 0.4 cc samples from the headspace followed by detection on a Packard Series 802 chromatograph (Packard, Downers Grove, Ill.) containing a Poropak N column and a thermal conductivity detector. All hydrogenase activity measurements in cell extracts were determined at 30° C.

In vivo hydrogenase activity of growing cells was measured by the tritium exchange assay described by Schink, Lupton and Zeikus (7). Cells were first grown to the midexponential phase in anaerobic pressure tubes that contained LPBB medium, 0.05% yeast extract, 0.5% carbon source and a $N_2$-$CO_2$ (95:5) gas headspace. Then, 6.5 μCi tritium gas was added (26 μCi/ml) and the cultures were shaken at 30° C. Liquid samples (0.25 ml) were removed by syringe at 10 min. intervals and tritiated water formation was quantified by liquid scintillation counting techniques.

RESULTS

Table 1 shows that *P. arboris* contained a methyl viologen linked uptake hydrogenase in cell extracts. The activity levels of this enzyme in cells were related to the carbon substrates fermented and increased amounts were detected on lactate versus glucose and highest levels on fumarate as the energy source. The uptake hydrogenase assayed in lactate grown cells also coupled to the reduction of other dyes, but less activity was detected with the more oxidized electron acceptors, dichlorophenol indophenol or methylene blue than with methyl or benzyl viologen. No activity was detected with NAD as electron acceptor; and, the low levels of NADP reduction observed is considered a result of indirect coupling caused by the presence of a ferredoxin-NADP oxidoreductase activity in cell extracts (data not shown). The addition of CO to the cuvette headspace inhibited uptake hydrogenase activity by greater than 94%.

Table 2 illustrates that cell extracts of *P. arboris* contained a production hydrogenase activity which was dependent on dithionite-reduced methyl viologen as electron donor. Reduced *C. pasteurianum* ferredoxin also substituted as the electron donor for hydrogen production in extracts treated to remove endogenous electron carrier, but the activity levels were lower than those observed in untreated cell extracts.

The detection of reversible hydrogenase activity in cell extracts initiated a series of experiments aimed at assessment of the enzymes' physiological function in *P. arboris*. It was shown that the reversible hydrogenase was active during growth of *P. arboris* on either lactate or glucose as the sole carbon and energy source because tritiated $H_2$ was readily exchanged into water. In another experiment it was shown that during growth of the organism on glucose, trace amounts of hydrogen were produced in the exponential phase and later completely consumed in the stationary growth phase. The same hydrogen recycling process was observed during growth on lactate.

The effect of exogenous hydrogen addition on growth and acid production when *P. arboris* was grown on either glucose, lactate or fumarate as the fermentable carbohydrate is shown in Table 3. The presence of one atmosphere $H_2$ had no significant effect on the doubling time of *P. arboris* grown on glucose. However, hydrogen addition dramatically altered the ratio of propionate to acetate formed but not the total amount of acids made from lactate, fumarate or glucose fermentations. The presence of 2 atmospheres of hydrogen changed the final propionate to acetate ratio from 2:1 (no $H_2$ added) to 16:1 and propionate was formed as virtually the sole end product of glucose fermentation. In addition, higher partial pressures of exogenous hydrogen correlated with larger decreases in acetate production from glucose fermentation.

The above results provide the first evidence for the following features of propionate producing bacteria: (1) the presence of reversible hydrogenase activity in cell extracts of a nitrogen-fixing species; (2) the production and consumption of hydrogen during growth on carbohydrates; (3) a hydrogen dependent homopropionate fermentation of glucose; and (4) utilization and regulation of hydrogenase to control the direction of intracellular carbon and electron flow during propionate fermentations.

Hydrogenase functions in *P. arboris* to control the flow of carbon and electrons during growth and propionate production. During growth on lactate or glucose alone, intermediary reduced electron carriers and pyruvate are formed which are then converted into a 2:1 ratio of propionate/acetate but in association with a hydrogen recycling process. The function of reversible hydrogenase under these fermentation conditions is to prevent over-reduction of ferredoxin which could inhibit pyruvate oxidation and acetate formation, a transformation that is linked to the generation of reducing equivalents needed for propionate production. Under these conditions, hydrogen is produced as a redox sink and it can be reconsumed by hydrogenase when the intracellular carriers become less reduced. Excess exogenous hydrogen dramatically alters carbon and electron flow during glucose and lactate fermentation by preventing pyruvate transformation into acetate, $CO_2$ and $H_2$. Under these conditions, hydrogenase functions in uptake as a key electron donating reaction and this explains how a homopropionate fermentation of glucose can be achieved with *P. arboris*.

The regulation of hydrogenase levels observed in relation to organic substrates fermented by *P. arboris* is a novel finding. When paper calculations are made on an equivalent mole of acid formed basis, 1.5 glucose is fermented into propionate, acetate and $CO_2$ in a 2:1:1 ratio; whereas, 3 fumarate can be fermented in a 2:1:4 ratio with 1 mol of substrate being oxidized into reducing equivalents needed to reduce the other 2 mol of substrate to propionate. The twenty-fold increase in activity level detected in fumarate versus glucose grown cells implies that a more significant catabolic role of hydrogenase is linked to reverse carbon and electron flow (i.e., oxidation of fumarate) which is only associated with fumarate metabolism. This suggests but does not prove that during fumarate fermentation, electron consumption is limiting and electron flow may be inhibited by over-reduction of cellular electron carriers (Fd, NAD) with the concurrent need to shunt electrons to hydrogen. Therefore, more detailed studies on hydrogen metabolism during growth on fumarate are needed because higher pressures of $H_2$ may be formed via hydrogenase in order to control the redox state of ferredoxin so that electrons can flow to fumarate reductase. In different thermoanaerobic bacterial species which ferment carbohydrates, different electron flow patterns via regulation of the pyridine nucleotide ferredoxin oxidoreductases correlated with hydrogenase activity levels and the amounts of hydrogen produced; and, high levels of hydrogenase were associated with a flow of electrons from NADH to ferredoxin while the reverse was true for species with low enzyme activity (6).

TABLE 1

Relationship Between Growth Substrate, in vitro Electron Acceptors and Hydrogen Consumption Activity of *P. arboris* Cell Extracts[a]

| Growth Substrate | Electron Acceptor | Hydrogenase Activity (nmol $H_2$/min/mg protein) |
|---|---|---|
| Glucose | Methyl viologen | 150 |
| Fumarate | Methyl viologen | 2,570 |
| Lactate | Methyl viologen | 750 |
| Lactate | Benzyl viologen | 430 |
| Lactate | Dichlorophenol indophenol | 63 |
| Lactate | Methylene blue | 28 |
| Lactate | NADP | 40 |
| Lactate | NAD | 0.0 |

[a]Experimental Conditions: Anoxic cuvettes contained 1 ml tricine buffer (pH 8.0), electron acceptor and cell-free extract as indicated under a 100% $H_2$ headspace.

TABLE 2

Relationship Between Reaction Mixture Contents and Hydrogen Production Activity by Cell Extracts of *P. arboris* Grown on Lactate

| Condition | Hydrogenase Activity (nmol $H_2$/50 min/vial) |
|---|---|
| I. Untreated Extract | |
| Complete | 7,150 |
| methyl viologen | ≦50 |
| dithionite | ≦50 |
| extract | ≦50 |
| II. DEAE Cellulose Treated Extract | |
| Complete | 192 |
| ferredoxin | 56 |
| dithionite | ≦5 |
| extract | ≦5 |

[a]Experimental Conditions: Anoxic vials contained: 5 ml of tricine buffer (pH 8.0) and plus or minus 20 μmol dithionite. Experiment I also contained 20 μmol methyl viologen and 1.35 mg protein of untreated cell-free extract where indicated. Experiment II contained 100 μg *Clostridium pasteurianum* ferredoxin and 0.46 mg DEAE cellulose treated cell extract where indicated.

TABLE 3

Influence of Exogenous Hydrogen on Organic Substrate Fermentations of *P. arboris*[a]

| Substrate | Doubling Time (hours) | Final Acid Product Concentration (mM) Acetate | Final Acid Product Concentration (mM) Propionate | Propionate Acetate Ratio (mM/mM) |
|---|---|---|---|---|
| Sodium Lactate | — | 5.4 | 13.5 | 2.8 |
| Sodium Lactate + $H_2$ (1 atm) | — | 3.0 | 16.0 | 5.3 |
| Sodium Fumarate | — | 6.5 | 13.8 | 2.1 |
| Sodium Fumarate + $H_2$ (1 atm) | — | 2.6 | 17.4 | 6.7 |
| Glucose | 4.36 | 5.9 | 11.2 | 2.1 |
| Glucose + $H_2$ (1 atm) | 4.19 | 1.6 | 13.0 | 8.1 |
| Glucose + $H_2$ (2 atm) | — | 0.8 | 12.6 | 16.1 |

[a]Experimental Conditions: Cultures were grown in 158 ml serum vials with 50 ml LPBB medium supplemented with 0.05% yeast extract and 0.5% of the substrate indicated. $H_2$ when present, was added as an overpressure to the headspace after inoculation. The glucose cultures were shaken, the lactate and fumarate cultures were static. Cultures were incubated at 30° C. and end products analyzed at the end of growth.

The discovery that propionate-forming bacteria can use hydrogen as a catabolic electron donor is important to applied and environmental microbiology. Thus, in anaerobic ecosystems such as biogas digestors, the rumen, wetwoods or aquatic sediments, the propionate bacteria represent a newly recognized group of $H_2$ consuming bacteria along with the methanogens, acetogens and sulfidogens (8). These bacteria may be responsible for hydrogen consumption under particular environmental conditions such as in mild acidic environments or those low in sulfate and fixed nitrogen. Propionate is also a potential chemical product of biomass fermentation (9); and, now the maximal theoretical yield from glucose may be achieved in industrial fermentations with species like *P. arboris* and without waste carbon production (i.e., acetate or $CO_2$) provided that $H_2$ is supplied as reductant.

The references which follow are incorporated by reference herein.

REFERENCES

[1] Baranova, N. A. and Gogatova, I. N. (1974) Microbiologyia, Vol. 43, No. 5, p. 791-794. (Microbiology, English Translation, 1975 p. 675-678).

[2] Adams, M. W. W., Mortenson, L. E. and J. S. Chen (1981) Biochemica Biophysica Acta. Vol. 594, p. 105-176.

[3] Schink, B., Thompson, T. E. and Zeikus, J. G. (1982) J. Gen. Microbiol. 128, 2771-2779.

[4] Kerby, R., Niemczura, W., and Zeikus, J. G. (1983) J. Bacteriol 155, 1208-1218.

[5] Zeikus, J. G., Fuchs, G., Kenealy, W., and Thauer, R. K. (1977) J. Bacteriol. 132, 604-613.

[6] Lamed, R. and Zeikus, J. G. (1980) J. Bacteriol. 144, 569-578.

[7] Schink, B., Lupton, F. S. and Zeikus, J. G. (1983) Appl. Environ. Microbiol. 45, 1491-1500.

[8] Zeikus, J. G. (1983) Microbes in Their Natural Environments, Soc. Gen. Microbiol., Cambridge University Press.

[9] Zeikus, J. G. (1980) Ann. Rev. Microbiol. 34, 423-464.

What is claimed is:

1. In the method of producing propionate or propionic acid which comprises cultivating a propionic acid-producing bacterium having the identifying characteristics of *Propionispira arboris* ATCC No. 33732 which produces a reversible hydrogenase and converts carbohydrates first to pyruvate and then the pyruvate to acetate, carbon dioxide and propionic acid or propionate under anaerobic conditions in a medium which contains a simple carbohydrate substrate, essential minerals, vitamins and growth factors, the improvement which comprises employing an overpressure of hydrogen effective to cause the hydrogenase produced by the bacterium to suppress the conversion of the pyruvate to acetate and carbon dioxide and to promote the formation of propionate or propionic acid.

2. A method of claim 1 in which the substrate is a simple sugar.

3. A method of claim 1 in which the substrate is fumarate.

4. A method of claim 1 in which the substrate is lactate.

5. A method of claim 1 in which the substrate is glucose and the overpressure of hydrogen is one atmosphere.

6. A method of claim 1 in which the substrate is glucose and the overpressure of hydrogen is two atmospheres.

7. A method of claim 1 in which the substrate is fumarate and the overpressure of hydrogen is one atmosphere.

8. A method of claim 1 in which the substrate is lactate and the overpressure of hydrogen is one atmosphere.

* * * * *